United States Patent [19]

Church et al.

[11] 4,288,602
[45] Sep. 8, 1981

[54] SELECTIVE OXIDATION OF 1,2-DIPHENYL-4-(2-PHENYLTHIO)ETHYL)-3,5-PYRAZOLIDINEDIONE TO THE SULFINYL COMPOUND

[75] Inventors: George A. Church, Dorval; Chih H. Chou, Dollard des Ormeaux, both of Canada

[73] Assignee: American Home Products Corporation, New York, N.Y.

[21] Appl. No.: 136,147

[22] Filed: Mar. 31, 1980

[51] Int. Cl.$^3$ .......................................... C07D 231/63
[52] U.S. Cl. ................................................... 548/361
[58] Field of Search ....................................... 548/361

[56] References Cited
U.S. PATENT DOCUMENTS 2,700,671  1/1955  Häflinger ............................ 548/361
3,257,403  6/1966  Pfister et al. ........................ 548/361

OTHER PUBLICATIONS

Pfister et al., Helv. Chim. Acta 1961, vol. 44, pp. 232–237.
Gragerov et al., Zh. Obshch. Khim, 1963, vol. 33, p. 543.
Tagaki et al., Chemistry and Industry (London), 1964, pp. 1624–1626.
Gragerov et al., Chem. Abst. 1963, vol. 58, p. 13831b.

Primary Examiner—Alan L. Rotman
Assistant Examiner—Natalia Harkaway
Attorney, Agent, or Firm—Adley F. Mandel

[57] ABSTRACT

Herein is described a process for oxidizing 1,2-diphenyl-4-[2-(phenylthio)ethyl]-3,5-pyrazolidinedione with peroxymonosulfuric acid to obtain 1,2-diphenyl-4-[2-(phenylsulfinyl)ethyl]-3,5-pyrazolidinedione.

5 Claims, No Drawings

SELECTIVE OXIDATION OF 1,2-DIPHENYL-4-(2-PHENYLTHIO)ETHYL)-3,5-PYRAZOLIDINEDIONE TO THE SULFINYL COMPOUND

BACKGROUND OF THE INVENTION

This invention describes a novel and useful process for oxidizing 1,2-diphenyl-4-[2-(phenylthio)ethyl]-3,5-pyrazolidinedione with peroxymonosulfuric acid to obtain 1,2-diphenyl-4-[2-(phenylsulfinyl)ethyl]-3,5-pyrazolidinedione. The latter compound is useful as an uricosuric agent.

An oxidation of 1,2-diphenyl-4-[2-(phenylthio)ethyl]-3,5-pyrazolidinedione using hydrogen peroxide is described by R. Pfister and F. Hafliger, Helv. Chim. Acta, 44, 232 (1961). Although the latter report describes the preparation of 1,2-diphenyl-4-[2-(phenylsulfinyl)ethyl]-3,5-pyrazolidinedione in reasonable yield, hydrogen peroxide is not suitable as an oxidizing agent when a number of large scale reactions have to be performed. In large scale preparations, use of hydrogen peroxide gives unpredictable yields of the sulfinyl compound, sometimes unacceptably low. Furthermore, with hydrogen peroxide, a major side reaction is the concurrent oxidation of the sulfoxide to the corresponding sulfone which is very difficult to remove. Several other oxidizing agents, for example, N-bromosuccinimide, sodium metaperiodate, chromic acid-pyridine, chromic acid-glacial acetic acid, perbenzoic acid and manganese dioxide, were tried. Each of these agents failed to produce the desired sulfinyl compound. Although m-chloroperbenzoic acid, when used as the oxidizing agent, gave the sulfinyl compound in reasonable yield, m-chloroperbenzoic acid is not acceptable because of its high cost.

Surprisingly, use of peroxymonosulfuric acid, also known as Caro's acid, as the oxidizing agent gave consistent and acceptable yields (about 60%) of the desired sulfinyl compound and very small amounts of the undesired sulfone (less than 5%). Furthermore, Caro's acid is a very inexpensive oxidizing agent.

The effectiveness of Caro's acid as an oxidizing agent is unexpected. More explicitly, diphenyl sulfide has been oxidized by Caro's acid to give diphenyl sulfoxide in 39% yield by I. P. Gragerov and A. F. Levit, Zh. Obshch. Khim., 33, 543 (1963). Diphenyl sulfide is a typical aromatic sulfide. The starting material used in this invention also is an aromatic sulfide and would be expected to behave as a typical aromatic sulfide; however, it does not. Most aromatic sulfides can be oxidized in 70% dioxane in water to the corresponding sulfoxide with an equivalent amount of N-bromosuccinimide. On the other hand, the reaction of N-bromosuccinimide with alkyl sulfides gives no sulfoxides, W. Tagaki et al., Chemistry and Industry (London), September 19, 1964, p 1624. The starting sulfide used in this invention failed to be oxidized to the sulfinyl compound under similar conditions using N-bromosuccinimide. Thus, the lack of reactivity of 1,2-diphenyl-4-[2-(phenylthio)ethyl]-3,5-pyrazolidinedione, when compared to typical aromatic sulfides, would predict that oxidation of the starting sulfide used in this invention with Caro's acid should give very low yields of the corresponding sulfinyl compound. However, the reverse was discovered, Caro's acid is an effective and safe oxidizing agent for selectivity converting 1,2-diphenyl-4-[2-(phenylthio)ethyl]-3,5-pyrazolidinedione to the corresponding sulfinyl compound.

SUMMARY OF THE INVENTION

Herein is described a process for oxidizing 1,2-diphenyl-4-[2-(phenylthio)ethyl]-3,5-pyrazolidinedione with peroxymonosulfuric acid to obtain 1,2-diphenyl-4-[2-(phenylsulfinyl)ethyl]-3,5-pyrazolidinedione.

DETAILS OF THE PROCESS

The peroxymonosulfuric acid (Caro's acid) is prepared by stirring a mixture of potassium persulfate with about 0.26 molar equivalents of conc. sulfuric acid until a homogenous paste is obtained. To the paste, about 20 molar equivalents of cold water is slowly added. After stirring for about one hour, the resulting solution of Caro's acid is ready for use as an oxidizing agent.

Oxidation of 1,2-diphenyl-4-[2-(phenylthio)ethyl]-3,5-pyrazolidinedione with the above solution of Caro's acid gives 1,2-diphenyl-4-[2-(phenylsulfinyl)ethyl]-3,5-pyrazolidinedione. With respect to 1,2-diphenyl-4-[2-(phenylthio)ethyl]-3,5-pyrazolidinedione, about 1.0 to 2.0 molar equivalents, preferably 1.3 to 1.5 molar equivalents, of Caro's acid is required. These amounts of Caro's acid are based upon the potassium persulfate used to make up the Caro's acid. When performing the oxidation, a solvent is used to dissolve the starting material, 1,2-diphenyl-4-[2-(phenylthio)ethyl]-3,5-pyrazolidinedione. Suitable solvents are inert water miscible solvents; for example, lower alkanols containing up to four carbon atoms and lower alkanoic acids containing two to four carbon atoms, or mixtures thereof. A useful solvent is acetic acid which can be used in amounts ranging from about 100 to 200 molar equivalents of acetic acid with respect to the starting material. The starting material is first dissolved in the glacial acetic acid and then the Caro's acid is added. The solution of 1,2-diphenyl-4-[2-(phenylthio)ethyl]-3,5-pyrazolidinedione, aqueous Caro's acid and acetic acid is allowed to react until the oxidation is complete and 1,2-diphenyl-4-[2-(phenylsulfinyl)ethyl]-3,5-pyrazolidinedione is formed. Usually, the solution is maintained at about 0° to 30° C., preferably 5° to 25° C., for about 10 to 30 hours. From the solution, 1,2-diphenyl-4-[2-(phenylsulfinyl)ethyl]-3,5-pyrazolidinedione is isolated in a conventional manner, for example, decomposition of excess Caro's acid, extraction and crystallization.

The following examples illustrate further the invention.

EXAMPLE 1

Preparation of Caro's Acid

To 20 g (0.074 moles) of finely ground potassium persulfate ($K_2S_2O_8$), 15 ml of conc. sulfuric acid was added with stirring until a homogenous paste was obtained. Next, 260 ml of ice cold water was added (very exothermic) and the solution was stirred for one hour to obtain a solution of Caro's acid.

EXAMPLE 2

Oxidation of 1,2-Diphenyl-4-[2-(phenylthio)ethyl]-3,5-pyrazolidinedione 1,2-Diphenyl-4-[2-(phenylthio)ethyl]-3,5-pyrazolidinedione (20 g, 0.052 moles) was dissolved in 400 ml of glacial acetic acid. To this solution, 240 ml of Caro's acid solution (described in Example 1) was added dropwise over a 30 minute period. A TLC taken three hours after the addition was begun showed starting material. The remainder of the Caro's acid solution was added and the reaction mixture was kept at 5° C. for eighteen hours. Thereafter, the reaction mixture was stirred for two more hours while it came to room temperature. TLC showed no starting material. A 5% sodium bisulfite solution (200 ml) was added to the reaction mixture followed by the addition of 300 ml of ethyl acetate. Water (500 ml) and 300 ml more of ethyl acetate were added. The layers were separated and the organic layer was washed with 500 ml of 5% sodium bicarbonate solution. The solvent was evaporated under reduced pressure and toluene (150 ml) was added. The toluene was removed by evaporation under reduced pressure to give a residue (20.2 g). The residue was crystallized from ethanol (60 ml) to give 9.7 g of 1,2-diphenyl-4-[2-(phenylsulfinyl)ethyl]-3,5-pyrazolidinedione. The mother liquors were concentrated to give another 2.8 g of the sulfinyl compound (total 12.5 g, 60% of theory). The sulfinyl compound exhibited the following characteristics: mp 130°–131.5° C.; nmr(CDCl$_3$)$\delta$ 2.45 (m, 2H), 3.3 (m, 3H), 7.25 (m, 10H) and 7.5 (m, 5H); and Anal. Calcd for C$_{23}$H$_{20}$O$_3$N$_2$S: C, 68.30% H, 4.99% N, 6.93% and Found: C, 67.94% H, 5.09% N, 6.84%.

We claim:

1. A process for preparing 1,2-diphenyl-4-[2-(phenylsulfinyl)ethyl]-3,5-pyrazolidinedione, with only very small amounts of the undesired corresponding sulfone, which comprises oxidizing 1,2-diphenyl-4-[2-(phenylthio)ethyl]-3,5-pyrazolidinedione with peroxymonosulfuric acid.

2. A process of claim 1 wherein 1,2-diphenyl-4-[2-(phenylthio)ethyl]-3,5-pyrazolidinedione is oxidized with peroxymonosulfuric acid in a solution of aqueous acetic acid.

3. A process of claim 1 wherein said process is conducted at about 0° to 30° C. with about 1.0 to 2.0 molar equivalents of peroxymonosulfuric acid with respect to 1,2-diphenyl-4-[2-(phenylthio)ethyl]-3,5-pyrazolidinedione.

4. A process of claim 1 wherein said process is conducted at about 5° to 25° C. with about 1.3 to 1.5 molar equivalents of peroxymonosulfuric acid with respect to 1,2-diphenyl-4-[2-(phenylthio)ethyl]-3,5-pyrazolidinedione.

5. A process of preparing 1,2-diphenyl-4-[2-(phenylsulfinyl)ethyl]-3,5-pyrazolidinedione, with only very small amounts of the undesired corresponding sulfone, which comprises oxidizing 1,2-diphenyl-4-[2-(phenylthio)ethyl]-3,5-pyrazolidinedione with about 1.3 to 1.5 molar equivalents of peroxymonosulfuric acid, with respect to said 1,2-diphenyl-4-[2-(phenylthio)ethyl]-3,5-pyrazolidinedione, in a solution of aqueous acetic acid at about 5° to 25° C.

* * * * *